(12) United States Patent
van de Lavoir et al.

(10) Patent No.: US 9,644,178 B2
(45) Date of Patent: *May 9, 2017

(54) METHOD FOR CULTURING AVIAN GONOCYTES

(71) Applicant: Crystal Bioscience Inc., Emeryville, CA (US)

(72) Inventors: Marie-Cecile van de Lavoir, San Francisco, CA (US); Robert Etches, San Mateo, CA (US)

(73) Assignee: CRYSTAL BIOSCIENCE, INC., Emeryville, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/488,185

(22) Filed: Sep. 16, 2014

(65) Prior Publication Data

US 2015/0082471 A1    Mar. 19, 2015

Related U.S. Application Data

(63) Continuation of application No. 12/986,868, filed on Jan. 7, 2011, now Pat. No. 8,865,462.

(60) Provisional application No. 61/296,803, filed on Jan. 20, 2010.

(51) Int. Cl.
| | |
|---|---|
| *C12N 5/00* | (2006.01) |
| *A01K 67/027* | (2006.01) |
| *C12N 5/076* | (2010.01) |
| *C12N 5/0735* | (2010.01) |
| *C12N 5/073* | (2010.01) |
| *C12N 5/075* | (2010.01) |
| *C12N 15/85* | (2006.01) |
| *A61K 36/12* | (2006.01) |

(52) U.S. Cl.
CPC .......... *C12N 5/061* (2013.01); *A01K 67/0271* (2013.01); *C12N 5/0604* (2013.01); *C12N 5/0609* (2013.01); *C12N 5/0611* (2013.01); *C12N 15/85* (2013.01); *A01K 2227/30* (2013.01); *A61K 36/12* (2013.01); *C12N 2517/02* (2013.01)

(58) Field of Classification Search
USPC ............................................. 435/325; 800/19
See application file for complete search history.

(56) References Cited

U.S. PATENT DOCUMENTS

| | | | |
|---|---|---|---|
| 5,340,740 A * | 8/1994 | Petitte | ................. C12N 5/0606 435/349 |
| 5,545,806 A | 8/1996 | Lonberg et al. | |
| 5,545,807 A | 8/1996 | Surani et al. | |
| 5,625,126 A | 4/1997 | Lonberg et al. | |
| 5,633,425 A | 5/1997 | Lonberg et al. | |
| 5,656,479 A * | 8/1997 | Petitte | ................. C12N 5/0606 435/349 |
| 5,759,763 A | 6/1998 | Naito et al. | |
| 5,840,510 A | 11/1998 | Tanaka et al. | |
| 6,156,569 A * | 12/2000 | Ponce de Leon | .. A01K 67/0271 435/325 |
| 6,333,192 B1 * | 12/2001 | Petitte | ................. C12N 5/0606 435/325 |
| 6,500,668 B2 * | 12/2002 | Samarut | ............ A01K 67/0275 435/325 |
| 6,673,986 B1 | 1/2004 | Kucherlapati et al. | |
| 6,861,572 B1 | 3/2005 | Etches et al. | |
| 6,872,569 B2 | 3/2005 | Lee et al. | |
| 7,041,870 B2 | 5/2006 | Tomizuka et al. | |
| 7,049,426 B2 | 5/2006 | Green et al. | |
| 7,064,244 B2 | 6/2006 | Jakobovits et al. | |
| 7,129,084 B2 | 10/2006 | Buelow et al. | |
| 7,145,057 B2 | 12/2006 | Van De Lavoir | |
| 7,249,569 B2 | 7/2007 | Mendu et al. | |
| 7,323,618 B2 | 1/2008 | Zhu | |
| 7,418,922 B2 | 9/2008 | Wolfe et al. | |
| 7,422,897 B2 | 9/2008 | Petitte et al. | |
| 7,476,776 B2 | 1/2009 | Hat et al. | |
| 7,585,668 B2 | 9/2009 | Buelow et al. | |
| 7,617,795 B2 | 11/2009 | Wolfe et al. | |
| 2002/0028488 A1 | 3/2002 | Singh et al. | |
| 2002/0108132 A1 | 8/2002 | Rapp | |
| 2002/0138864 A1 | 9/2002 | Han et al. | |
| 2002/0162134 A1 | 10/2002 | Baguisi et al. | |
| 2003/0061629 A1 | 3/2003 | Sutrave | |
| 2003/0170888 A1 | 9/2003 | Van De Lavoir et al. | |
| 2003/0172387 A1 | 9/2003 | Zhu et al. | |
| 2003/0182675 A1 | 9/2003 | Etches et al. | |

(Continued)

FOREIGN PATENT DOCUMENTS

| | | | |
|---|---|---|---|
| KR | WO 0047717 | * | 8/2000 |
| WO | WO0047717 | | 8/2000 |
| WO | WO0212437 | | 2/2002 |

OTHER PUBLICATIONS

Ramathal ("Embryonic stem cells and the germ lineage," Chapt 21, Sep. 15, 2011, Michael S. Kallos ed, p. 391-424).*
Culty (Birth Defects Res., Part C, 2009, vol. 87, p. 1-26).*
Hamburger (J. Morphol., 1955, vol. 88, p. 49-92).*
Hong (Transgenic Research, 1998, vol. 7, p. 247-252).*
van de Lavoir (Nature, Jun. 2006, vol. 441, p. 766-769).*
Naito (Reprod. Res., 2007, vol. 134, p. 577-584).*
Mozdziak (Poultry Sci., 2006, vol. 85, p. 1764-1768).*
Gonocyte definition Wikipedia 2015.*

(Continued)

*Primary Examiner* — Michael Wilson
(74) *Attorney, Agent, or Firm* — James S. Keddie; Bozicevic, Field & Francis LLP

(57) ABSTRACT

A sustained culture of isolated avian gonocytes is provided, as well as a method of making and using the same. A chimeric avian containing an isolated gonocyte and a transgenic avian produced using the chimeric avian are also provided. The cell and method may be employed to make, among other things, transgenic avian that produce a heterologous protein, e.g., a therapeutic protein.

21 Claims, 3 Drawing Sheets

(56) References Cited

U.S. PATENT DOCUMENTS

| | | |
|---|---|---|
| 2004/0226058 A1 | 11/2004 | De Leon et al. |
| 2005/0114916 A1 | 5/2005 | Etches et al. |
| 2005/0246782 A1 | 11/2005 | Etches et al. |
| 2005/0282273 A1 | 12/2005 | Swiatek |
| 2006/0026696 A1 | 2/2006 | Buelow et al. |
| 2006/0053504 A1 | 3/2006 | Zhu et al. |
| 2006/0110824 A1 | 5/2006 | Chen et al. |
| 2006/0174362 A1 | 8/2006 | Van De Lavoir et al. |
| 2006/0174363 A1 | 8/2006 | Van De Lavoir et al. |
| 2006/0191026 A1 | 8/2006 | Zhu et al. |
| 2006/0206952 A1 | 9/2006 | Van De Lavoir et al. |
| 2007/0092505 A1 | 4/2007 | Buelow et al. |
| 2009/0060908 A1 | 3/2009 | Cardarelli et al. |
| 2009/0083871 A1 | 3/2009 | Etches et al. |
| 2009/0083872 A1 | 3/2009 | Etches et al. |
| 2009/0165155 A1 | 6/2009 | Zhu et al. |
| 2010/0138946 A1 | 6/2010 | Van De Lavoir et al. |
| 2010/0192241 A1 | 7/2010 | Etches et al. |
| 2011/0023160 A1 | 1/2011 | Etches et al. |
| 2011/0028696 A1 | 2/2011 | Cardarelli et al. |
| 2011/0055938 A1 | 3/2011 | Harriman et al. |
| 2011/0179510 A1 | 7/2011 | Van De Lavoir et al. |
| 2011/0277048 A1 | 11/2011 | Etches et al. |
| 2011/0296541 A1 | 12/2011 | Etches et al. |
| 2014/0289880 A1* | 9/2014 | Van de Lavoir ... A01K 67/0275 800/19 |

OTHER PUBLICATIONS

Carsience, et al., "Germline chimeric chickens from dispersed donor blastodermal cells and compromised recipient embryos", Development 117, pp. 669-675, 1993.

Culty Gonocytes, the forgotten cells of the germ cell lineage, Birth Defects Res C Embryo Today, 2009, 87:1-26.

Definition of sustain, 2013.

DeLavoir, et al., "Germline transmission of genetically modified primordial germ cells", Nature, 2006, 441:766-9.

De Rooij, et al., "All you wanted to know about spermatogonia but were afraid to ask", J Androl, 2000, 21:776-98.

Goel, et al., "Multipotential ability of primitive germ cells from neonatal pig testis cultured in vitro", Reprod Fertil Dev, 2009, 21:696-708.

Han (Theriogenology, 2002, vol. 58, p. 1531-1539).

Leighton, et al., "Genetic modification of primordial germ cells by gene trapping, gene targeting, and phiC31 integrase", Mol Reprod & Dev, 2008, 75:1163-75.

Ll, et al., "Genetic Variability in White Leghorns Revealed by Chicken Liver Expressed Sequence Tags", Poult Sci.,77:134-9, 1998.

Love, et al., "Transgenic Birds by DNA Microinjection", Biotechnology, 1994, 12:60-3.

Medical dictionary definition of "gonocyte", 2013.

Merriam Webster dictionary definition of "gonocyte", 2013.

Mondofacto dictionary definition of "gonocyte" 2013.

Mozdziak "Production of chick germline chimeras from fluorescence-activated cell-sorted gonocytes", Poult Sci., 2006, 85:1764-8.

Naito, "Testicular and ovarian gonocytes from 20-day incubated chicken embryos contribute to germline lineage after transfer into bloodstream of recipient embryos", Reproduction, 2007, 134:577-84.

Ponsuksili, et al., "Evaluation of Genetic Variation Within and Between Different Chicken Lines by DNA Fingerprinting", Oxford Journals, Life Sciences, Journal of Heredity, 89:17-23, 1998.

Schuman, et al., "Potential genetic modifications in the chicken", *Gallus domesticus*. In: Proceedings of the 2nd World Congress on Genetics Applied to Livestock Production, 1982, 6:157-63.

Scott, et al., "Generation of tissue-specific transgenic birds with lentiviral vectors", Proc Natl Acad Sci, 2005, 102:16443-7.

Vanhala, et al., "Evaluation of Genetic Variability and Genetic Distances Between Eight Chicken Lines Using Microsatellite Markers", Poult. Sci., 77:783-90, 1998.

Song, et al "Method for Culturing Avian Gonocytes", Biology of Reproduction, (2014),90(1):15, 1-8.

* cited by examiner

An quail ovary is colonized by GFP-expressing chicken gonocytes taken from a sustained culture. At 12 days of development, the GFP expressing progeny of the GFP expressing gonocytes are revealed by fluorescence microscopy.

An quail testis is colonized by GFP-expressing chicken gonocytes taken from a sustained culture. At 12 days of development, the GFP expressing progeny of the GFP expressing gonocytes are revealed by fluorescence microscopy.

METHOD FOR CULTURING AVIAN GONOCYTES

CROSS-REFERENCING

This application is a continuation of U.S. patent application Ser. No. 12/986,868, filed on Jan. 7, 2011 and claims the benefit of U.S. provisional patent application Ser. No. 61/296,803, filed Jan. 20, 2010, all of which are incorporated by reference herein in their entirety.

BACKGROUND

Cells that retain their capacity to contribute to the germline of vertebrates can be used to make transgenic animals, to cryopreserve the genome and to make germline chimeras. In mice, embryonic stem cells have been used to make transgenic animals and to cryopreserve specific strains that are of interest to the biomedical research community. In chickens, primordial germ cells (PGCs) have been cultured for extended periods of time, their genome has been modified and they have been used to make germline chimeras.

In vertebrates, the germline is separated from the somatic tissues at an early stage of development. In birds, the germline may be separated after only a few cell divisions whereas in mice, PGCs are derived from the proximal epiblast cells around 7.2 dpc. During the course of gastrulation the murine PGCs move through the posterior primitive streak into the extra-embryonic region. Around 8.5 dpc the PGCs will migrate back into the embryo proper following a route through the gut mesentery and become incorporated into the somatic component of the developing gonad. In males, PGCs are incorporated into the developing seminiferous tubules and in females, they are incorporated into the ovarian cortex.

In birds, PGCs descend through the epiblast and are swept into the anterior extra-embryonic region known as the germinal crescent. This process is underway when the egg is laid (at approximately Stage XII using the staging system of Eyal-Giladi and Kochav Developmental Biology (1976) 49, 321-337)) and is completed by 18 hours of development (about Stage 4 to 5 using the staging system of Hamburger and Hamilton (Journal of Morphology (1955) 88, 49-92). From the germinal crescent, PGCs migrate into the nascent vascular system and travel to the gonadal ridge where they exit into the developing testis or ovary.

The migratory property which defines PGCs ends when they take up residence in the undifferentiated gonad. At this time, they are referred to as gonocytes to reflect their status as the primary germ cells in the gonadal environment. Gonocytes have a distinct gene expression profile that is reflected in their unique response to various effectors.

Certain aspects of this disclosure relate to a culture method for producing avian gonocytes, avian gonocytes produced by the method and methods for using the same.

SUMMARY

A sustained culture of isolated avian gonocytes is provided, as well as a method of making and using the same. A chimeric avian containing an isolated gonocyte and a transgenic avian produced using the chimeric avian are also provided. The cell and method may be employed to make, among other things, transgenic avians that produce a heterologous protein, e.g., a therapeutic protein.

DEFINITIONS

Figure 1:
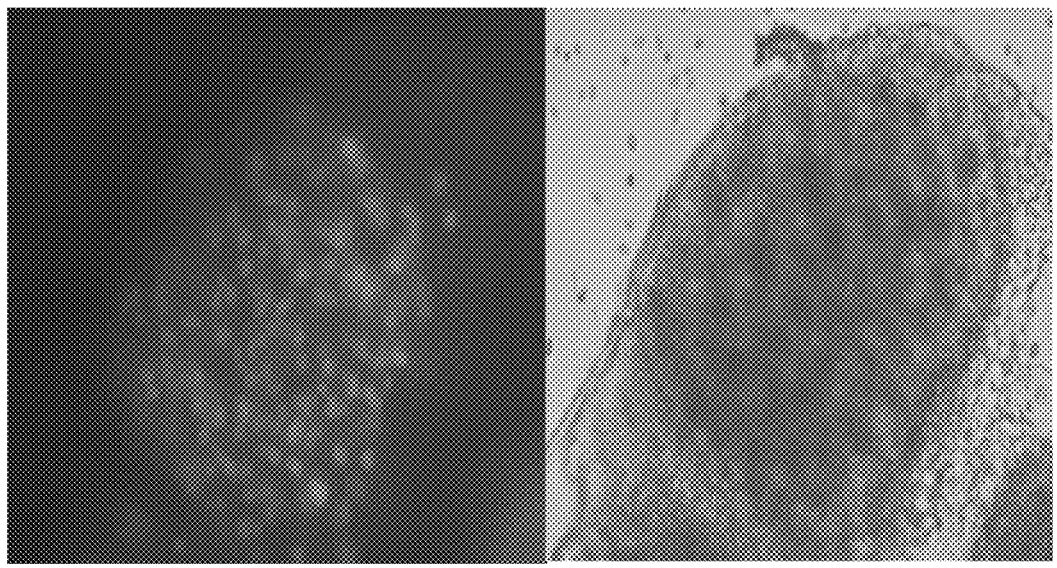
FIG. 1. shows an image of a male gonad at 7 days of development that was injected on day 3 with gonocytes grown in culture and transfected with GFP. Left panel is viewed under fluorescence incident light with a FITC filter and the right panel is viewed under bright light.

The terms "determining", "measuring", "evaluating", "assessing" and "assaying" are used interchangeably herein to refer to any form of measurement, and include determining if an element is present or not. These terms include both quantitative and/or qualitative determinations. Assessing may be relative or absolute. "Determining the presence of" includes determining the amount of something present, as well as determining whether it is present or absent.

The term "gene" refers to a nucleic acid sequence comprised of a promoter region, a coding sequence, and a 3'UTR.

The terms "protein" and "polypeptide" are used interchangeably herein.

The term "nucleic acid" encompasses DNA, RNA, single stranded or double stranded and chemical modifications thereof. The terms "nucleic acid" and "polynucleotide" are used interchangeably herein.

The term "operably-linked" refers to the association of nucleic acid sequences on a single nucleic acid fragment so that the function of one is affected by the other. For example, a promoter is operably-linked with a coding sequence when it is capable of affecting the expression of that coding sequence (i.e., the coding sequence is under the transcriptional control of the promoter). Similarly, when an intron is operably-linked to a coding sequence, the intron is spliced out of the mRNA to provide for expression of the coding sequence. "Unlinked" means that the associated genetic elements are not closely associated with one another and the function of one does not affect the other.

The term "homozygous" indicates that identical alleles reside at the same loci on homologous chromosomes. In contrast, "heterozygous" indicates that different alleles reside at the same loci on homologous chromosomes. A transgenic animal may be homozygous or heterozygous for a transgene.

The term "endogenous", with reference to a gene, indicates that the gene is native to a cell, i.e., the gene is present at a particular locus in the genome of a non-modified cell. An endogenous gene may be a wild type gene present at that locus in a wild type cell (as found in nature). An endogenous gene may be a modified endogenous gene if it is present at the same locus in the genome as a wild type gene. An example of such a modified endogenous gene is a gene into which a foreign nucleic acid is inserted. An endogenous gene may be present in the nuclear genome, mitochondrial genome etc.

The term "construct" refers to a recombinant nucleic acid, generally recombinant DNA, that has been generated for the purpose of the expression of a specific nucleotide sequence(s), or is to be used in the construction of other recombinant nucleotide sequences. A construct might be present in a vector or in a genome.

The term "recombinant" refers to a polynucleotide or polypeptide that does not naturally occur in a host cell. A recombinant molecule may contain two or more naturally-occurring sequences that are linked together in a way that does not occur naturally. A recombinant cell contains a recombinant polynucleotide or polypeptide. If a cell receives a recombinant nucleic acid, the nucleic acid is "exogenous" to the cell.

The term "selectable marker" refers to a protein capable of expression in a host that allows for ease of selection of those hosts containing an introduced nucleic acid or vector. Examples of selectable markers include, but are not limited to, proteins that confer resistance to antimicrobial agents (e.g., hygromycin, bleomycin, or chloramphenicol), proteins that confer a metabolic advantage, such as a nutritional advantage on the host cell, as well as proteins that confer a functional or phenotypic advantage (e.g., cell division) on a cell.

The term "expression", as used herein, refers to the process by which a polypeptide is produced based on the nucleic acid sequence of a gene. The process includes both transcription and translation.

The term "introducing" in the context of inserting a nucleic acid sequence into a cell, includes "transfection" and "transformation" and all other methods of introducing a nucleic acid into a cell, where the nucleic acid sequence may be incorporated into the genome of the cell (e.g., chromosome, plasmid, plastid, or mitochondrial DNA) or converted into an autonomous replicon, or transiently expressed.

The term "coding sequence" refers to a nucleic acid sequence that once transcribed and translated produces a protein, for example, in vivo, when placed under the control of appropriate regulatory elements. A coding sequence as used herein may have a continuous ORF or might have an ORF interrupted by the presence of introns or non-coding sequences. In this embodiment, the non-coding sequences are spliced out from the pre-mRNA to produce a mature mRNA.

The term "introduced" in the context of inserting a nucleic acid sequence into a cell, means "transfection", or "transformation", or "transduction" and includes reference to the incorporation of a nucleic acid sequence into a eukaryotic or prokaryotic cell wherein the nucleic acid sequence may be present in the cell transiently or may be incorporated into the genome of the cell (e.g., chromosome, plasmid, plastid, or mitochondrial DNA), converted into an autonomous replicon.

The term "plurality" refers to at least 2, at least 5, at least 10, at least 20, at least 50, at least 100, at least 200, at least 500, at least 1000, at least 2000, at least 5000, or at least 10,000 or at least 50,000 or more. In certain cases, a plurality includes at least 10 to 50. In other embodiments, a plurality may be at least 50 to 1,000.

As used herein, the term "isolated", with respect to a cell, refers to a cell that is cultured in vitro. If an animal is described as containing isolated cells, then those isolated cells were cultured in vitro and then implanted into the animal.

As used herein, the term "sustained culture", with respect to a sustained culture of isolated gonocytes, refers to a population of cells that: a) are grown in vitro in a synthetic growth medium and b) are capable of undergoing cell division in the medium. The term "sustained culture" explicitly excludes a population of cells that have been directly isolated from an animal, without subsequent cell division on a synthetic tissue culture medium.

The phrase "in a medium" with respect to cell division or growth in a medium, is intended to encompass growth on top of the medium as well as growth in the medium.

As used herein, a "synthetic" growth medium refers to man-made medium that is not a living, multicellular organism. The term "synthetic growth medium" explicitly excludes living embryos.

As used herein, the term "gonocyte" refers to a germ cell in a differentiated gonad that is responsible for gametogenesis (i.e., spermatogenesis in males and oogenesis in females). Gonocytes include gametogonia (spermatogonia and oogonia), oocytes, ootids, and ova. The term "gonocyte" is intended to explicitly exclude primordial germ cells that are migrating and have not yet that have not yet taken up residence in an undifferentiated gonad.

As used herein, an "avian" is intended to encompass any bird including, but not limited to members of the order Galliformes, e.g., chicken and turkey and Anseriformes, e.g., duck or goose.

As used herein, the term "passaging" refers to the periodic transfer of cells from a first growth medium onto a freshly made second growth medium that may be identical to the first growth medium.

As used herein, the term "implanting" is intended to encompass direct (e.g., injection directly into a region) and indirect (e.g., systemic administration) methods by which cells are placed in a region of an embryo.

As used herein, a "chimeric" animal is an animal containing cells from at least two different animals. A chimeric animal may be made by implanting cells from one animal into an embryo of another animal. The implanted cells may be harvested from a sustained culture prior to incorporation into the host embryo. The embryo develops into an animal, and the resultant animal may contain cells from both animals. The animals that contribute cells to a chimeric animal may be of the same of different species (i.e., the chimera may be an "intra-specific chimera" or an "inter-specific chimera").

The term "progeny" or "off-spring" refers to any and all future generations derived and descending from a particular animal or cell. Thus, the progeny an animal of any successive generation are included herein such that the progeny, the F1, F2, F3, generations and so on are included in this definition.

A chimeric animal may have cells donated by another animal in the germline, in which case the progeny of the animal may be heterozygous for chromosomes in the donated cells. If the donated cells contain an exogenous nucleic acid (i.e., nucleic acid that is not endogenous to the cells), the progeny of the chimeric animal may be "transgenic", where a "transgenic" animal is an animal made up cells containing foreign nucleic acid (i.e., recombinant nucleic acid that is not native to the animal). The foreign nucleic acid molecule may be called a "transgene" herein.

Further definitions may be elsewhere in this disclosure.

DESCRIPTION OF EXEMPLARY EMBODIMENTS

Before the present subject invention is described further, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a cell" includes a plurality of cells and reference to "a candidate agent" includes reference to one or more candidate agents and equivalents thereof known to those skilled in the art, and so forth. It is further noted that the claims may be drafted to exclude any optional element. As such, this statement is intended to serve as antecedent basis for use of such exclusive terminology as "solely", "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Isolated Avian Gonocytes

As noted above, a sustained culture of isolated avian gonocytes is provided which, as noted above, comprises a population of cells that: a) are grown in vitro in a synthetic growth medium and b) are capable of undergoing cell division in the medium. Also as noted above, the term "sustained culture" explicitly excludes gonocytes that have been directly isolated from an avian without a subsequent cell division on a synthetic tissue culture medium to produce progeny gonocytes. Gonocytes that have been directly isolated from an avian without a subsequent cell division on a synthetic tissue culture medium to produce progeny gonocytes are described in Mozdziak et al, (*Production of chick germline chimeras from fluorescent-activated cell sorted gonocytes* Poultry Science 2006 85: 1764-1768) and Naito et al, (*Testicular and ovarian gonocytes from 20-day incubated chicken embryos contribute to germline lineage after transfer into bloodstream of recipient embryos* Reproduction 2007 134 577-584), for example, as well as in other publications.

In certain embodiments, the sustained culture may contain at least $10^4$ genetically identical cells (i.e., cells of the same genotype), e.g., at least $10^5$ genetically identical cells, at least $10^6$ genetically identical cells, up to $10^8$ genetically identical cells or $10^9$ or more genetically identical cells. Depending on how many different animal embryos were used to seed the initial culture and how the culture is grown and passaged (e.g., whether a single colony or multiple colonies are passaged to a fresh medium), the culture may contain multiple sub-populations of cells, where the cells in each sub-population are genetically identical to one another and the different sub-populations of cells contain genetically different cells.

Depending on whether a solid (which term encompasses solid and semi-solid media) or liquid growth medium are used, the isolated gonocytes may be present as a colony of genetically identical cells on solid growth medium, or they may be interspersed within a liquid medium. The culture of gonocytes are not adherent cells.

In some embodiments, the sustained culture comprises: a) isolated avian gonocytes; and b) a synthetic growth medium. In certain embodiments, the synthetic growth medium may contain a conditioned medium supplemented with serum and a feeder layer. In particular embodiments, the medium may contain i. knock-out DMEM (e.g., DMEM buffer that does not contain L-glutamine or HEPES), fetal bovine serum, avian serum, (buffalo rat liver) BRL cell conditioned medium, fibroblast growth factor, stem cell factor, non-essential amino acids, beta-mercapto-ethanol, glutamine, pyruvate and ii.a feeder layer of STO (Sim mouse fibroblasts resistant to 6-thioguanine and ouabain) or BRL (Buffalo Rat Liver) cells. Examples of such media are described in the references cited below.

In particular embodiments, avian gonocytes may be cultured on the same culture medium as used for culture of avian primordial germ cells, methods for which are well established. Examples of media suitable for culturing avian gonocytes are described in Allioli et al (*Use of retroviral vectors to introduce and express the beta-galactosidase marker gene in cultured chicken primordial germ cells* Dev Biol. 1994 165:30-7), Chang et al (*Proliferation of chick primordial germ cells cultured on stroma cells from the germinal ridge* Cell Biol. Int. 1995 19:143-9), Chang et al, (*Production of germline chimeric chickens by transfer of cultured primordial germ cells* Cell Biol. Int. 1997 21:495-9), Han et al (*Proteome analysis of chicken embryonic gonads: identification of major proteins from cultured gonadal primordial germ cells* Mol. Reprod. Dev. 2005 72:521-9), van de Lavoir et al, (*Germline transmission of genetically modified primordial germ cells* Nature 2006 441: 766-9) Shiue et al (*Establishment of the long-term in vitro culture system for chicken primordial germ cells* Reprod. Domest. Anim. 2009 44:55-61) and Park et al, (*Improved germline transmission in chicken chimeras produced by transplantation of gonadal primordial germ cells into recipient embryos* Biol. Reprod. 2003 68:1657-62). Cultured chicken primordial germ cells are also discussed in the following reviews: Kerr et al (Methods Enzymol. 2006

419:400-26), Petitte et al (Mech. Dev. 2004 121:1159-68) and Petitte et al (Poult Sci. 1997 76:1084-92).

In particular embodiments, the isolated gonocytes may be undergoing cell division in the culture, asynchronously, and the avian gonocytes may be maintainable in the culture for at least 2 weeks (e.g., for at least 4 weeks, for at least 2 months, at least 6 months or at least a year or more), by periodically passaging the cells to fresh culture medium.

In particular embodiments, the culture may be cryogenically frozen and, as such, may be in a frozen state at −80° C. or below (e.g., in liquid nitrogen). In these embodiments, the culture may contain cells that are suspended in a liquid that contains a cryoprotectant, e.g., glycerol, methanol or DMSO (e.g., 5%-15% DMSO), for example. A cryovial containing the culture in cryoprotective agent at room temperature may be inserted into a special freezing container, e.g., a Nalgene "Mr Frosty" container, which has been pre-chilled to refrigerator temperature. The freezing container may then be placed into a −70° C. freezer for a period of time. Then the cryovial may quickly removed from the freezing container, placed into a storage container, and plunged into liquid nitrogen for indefinite storage. After a period of time, the cells can be thawed, and used in, for example, a method that is described in greater detail below.

In certain embodiments, the isolated avian gonocytes cells in the culture are also capable of populating the germ line of a recipient avian embryo, which as noted above, may or may not be of the same species as the cells. Methods for implanting gonocytes into a recipient avian embryo are described in greater detail below.

The isolated avian gonocytes are also capable of being transfected with an exogenous nucleic acid to produce recombinant gonocyte cells that may be used to make chimeric and transgenic avians. Such methods are also described in greater detail below.

Culture Methods

A method of producing progeny gonocytes from an isolated avian gonocyte is provided. In general terms, this method includes isolating a gonocyte cell from the gonad of an avian embryo and culturing the gonocyte cell until the cell divides to produce progeny gonocyte cells. In some embodiments, the avian embryo may be a Stage 29-36 embryo using the staging system of Hamburger and Hamilton (Journal of Morphology (1955) 88, 49-92). In particular embodiments, the avian embryo may be a 6-10 day old chicken embryo, e.g., a 6-8 day old chicken embryo.

Suitable media for culturing the cells is described above and exemplified below. Depending on how long the gonocytes are cultured, the gonocyte cell may undergo a single cell division to produce at least one progeny cell. In particular embodiments, the progeny of the gonocyte cell may be periodically passaged onto fresh growth medium, thereby allowing at least 5, at least 10 or at least 20 rounds of cell division to occur. Depending on the culture medium used and other growth conditions, avian gonocytes may divide approximately every 36-60 hours, e.g., 48 hours, in the culture.

In particular embodiments, the method may further include introducing an exogenous nucleic acid into an isolated gonocyte to produce a recombinant gonocyte. In these embodiments, the isolated gonocyte cells are generally isolated from the culture medium, the exogenous nucleic acid is introduced into the cells, and the cells are replated on medium containing an agent (e.g., an antibiotic or other selective agent) to select for transfected cells. Exogenous nucleic acid may be introduced into an isolated gonocytes using any of a number of suitable methods, including, but not limited to: calcium phosphate precipitation, direct micro injection, viral (e.g., retroviral) infection, lipofection, particle gun delivery and electroporation. Suitable methods for introducing exogenous nucleic acid into an isolated gonocyte may be readily adapted from the primordial germ cell transfection methods described in: Naito et al, (*Testicular and ovarian gonocytes from 20-day incubated chicken embryos contribute to germline lineage after transfer into bloodstream of recipient embryos* Reproduction. 2007 134: 577-84), Hong et al, (*Improved transfection efficiency of chicken gonadal primordial germ cells for the production of transgenic poultry* Transgenic Res. 1998 7:247-52), Jeong et al (*Simple separation of chicken gonadal primordial germ cells with and without foreign genes* Cell Biol. Int. 2002 26:647-51), Vick et al (*Transgenic birds from transformed primordial germ cells* Proc. Biol. Sci. 1993 251:179-82, Perry et al (Transgenesis in chickens Transgenic Res. 1993 2:125-33), Pain et al (Chicken embryonic stem cells and transgenic strategies Cells Tissues Organs 1999 165:212-9) Naito et al (*Expression of exogenous DNA in the gonads of chimaeric chicken embryos produced by transfer of primordial germ cell transfected in vitro and subsequent fate of the introduced DNA* J. Reprod. Feral. 1998 113:137-43), Chang et al, (*Production of germline chimeric chickens by transfer of cultured primordial germ cells* Cell Biol. Int. 1997 21:495-9) and van de Lavoir et al, (*Germline transmission of genetically modified primordial germ cells* Nature 2006 441: 766-9).

In certain embodiments, the exogenous nucleic acid may contain a recombinant polynucleotide containing an expression cassette, i.e., a promoter, a polynucleotide encoding a protein, and a transcriptional terminator, where the expression cassette is sufficient for the production of the protein by an avian. The recombinant nucleic acid may integrate into the genome of the host cell, or it may be present in a vector that replicates autonomously from the genome. In certain embodiments, the polynucleotide encoding the protein may be codon optimized for expression of the protein in the avian host. In particular embodiments, the promoter may be a tissue specific promoter, e.g., a promoter that directs expression of the protein to a desired tissue, e.g., egg white, yolk, or muscle tissue, for example.

Method of Use

Also provided is a method that includes separating a population of avian gonocyte cells from the above-described sustained culture of avian gonocytes. The method may further include implanting the population of avian gonocyte cells into a recipient avian embryo. As noted above, the recipient avian embryo may be the same species as the avian gonocyte cells, or a different species to the avian gonocyte cells. Incubation of the recipient embryo may produce a chimeric avian composed of cells derived from the recipient embryo and cells derived from the implanted gonocytes. In particular embodiments, incubation of the embryo results in population of the germ line of the recipient avian embryo by the avian gonocytes. In embodiments in which the implanted avian gonocytes contain exogenous nucleic acid, the chimeric avian containing the implanted cells may be mated to another avian, and the resultant offspring may be transgenic for the exogenous nucleic acid. As such, in certain embodiments and as discussed above, prior to implanting the progeny gonocyte cells into a recipient embryo, a recombinant nucleic acid many be inserted into those cells. The method may also include obtaining transgenic offspring of the recipient avian embryo. Also as noted above, the method may also include freezing the population of avian gonocytes cells to produce frozen cells and storing said frozen cells.

Methods for implanting gonocytes into a recipient embryo to produce a germline chimera are described in, for example, Mozdziak et al, (*Production of chick germline chimeras from fluorescent-activated cell sorted gonocytes* Poultry Science 2006 85: 1764-1768), Naito et al, (*Testicular and ovarian gonocytes from 20-day incubated chicken embryos contribute to germline lineage after transfer into bloodstream of recipient embryos* Reproduction 2007 134 577-584). Chang et al (*Production of Germline Chimeric Quail by Transfer of Gonadal Primordial Germ Cells Preserved in Liquid Nitrogen* Jpn. Poult. Sci, 35: 321-328, 1998) and Kang et al (*Reproduction of wild birds via interspecies germ cell transplantation*. Biology of Reproduction 2008 79: 931-7).

Gonocytes may be implanted into a recipient embryo by, e.g., injection into the subgerminal cavity, injection into the germinal crescent, or by injection into the bloodstream, for example.

In one example, the gonocytes cells may be injected into the subgerminal cavity of a stage X chicken embryo using a procedure adapted from Petitte et al (*Production of somatic and germline chimeras in the chicken by transfer of early blastodermal cells* Development 1990 108:185-189) and Mozdziak et al (*Development of transgenic chickens expressing bacterial β-galactosidase* Dev. Dyn. 2003 226: 439-445). In this method, the embryos may be cultured in a surrogate chicken eggshell, followed by a surrogate turkey eggshell, until hatching, following procedures modified from Borwornpinyo et al (*Culture of chicken embryos in surrogate eggshells* Poult. Sci. 2005 84:1477-1482).

In another example, chicken eggs may be pre-treated with an injection of a busulfan emulsion into the yolk of embryos after 24 h of incubation, according to the methods by Song et al (*Production of germline chimeric chickens following the administration of a busulfan emulsion*. Mol. Reprod. Dev. 2005 70:438-444). After busulfan injection, the eggs may be returned to the incubators until they reach stage 17 (Hamburger, V., and H. L. Hamilton. 1951. A series of normal stages in the development of the chick embryo. J. Morphol. 88:49-67) when they are injected through the dorsal aorta with 600 to 3,500 gonocytes. After injection, the eggshells can be sealed, and the eggs returned to the incubator and maintained until hatching. Naito et al, supra, describes a method by which gonocytes are injected into the bloodstream of a recipient animal. Generally methods for implanting gonocytes are similar to those for implanting PGCs, which are known (see citations above).

In a further example, embryos at 3 d of incubation may be injected with 1,000 to 2,000 gonocytes into the germinal crescent. The injected embryos may be cultured in a surrogate turkey eggshell until hatching, following the procedures of Borwornpinyo et al. (*Culture of chicken embryos in surrogate eggshells*. Poult. Sci. 2005 84:1477-1482).

The resultant embryo containing implanted cells may be incubated to produce a chimeric bird containing germ-line cells that are derived from the implanted cells.

Utility

The above-described cells and methods may be employed to make, among other things, a transgenic avian. In one embodiment, the avian may produce, e.g., a heterologous protein, e.g., a therapeutic protein (i.e., a protein having a therapeutic biological activity) or a reporter protein. In certain embodiments, the heterologous protein may be produced in an egg of the avian, particularly egg white. The protein may be isolated from the egg and used in a method of treatment. In other embodiments, the transgenic avian may be engineered to provide improved characteristics, e.g., increased muscle, better texture, increased disease resistance, increased ability to digest phytate, etc., by, for example, over-expression of an endogenous protein, expression of an non-endogenous protein, or by inhibiting gene expression. The cells and method may also be employed to preserve an avian genotype, e.g., of an endangered or valuable avian, by freezing the isolated cells. The cells can be later thawed and implanted into an avian embryo to produce a chimeric avian containing the isolated cells, the progeny of which may contain the initial avian genotype.

Examples of therapeutic proteins that may be produced in an avian egg include: erythropoietin, cytokines such as interferon-α, interferon-β, interferon-γ, interferon-o, and granulocyte-CSF, GM-CSF, coagulation factors such as factor VIII, factor IX, and human protein C, antithrombin III, thrombin, soluble IgE receptor α-chain, IgG, IgG fragments, IgG fusions, IgM, IgA, interleukins, urokinase, chymase, and urea trypsin inhibitor, IGF-binding protein, epidermal growth factor, growth hormone-releasing factor, annexin V fusion protein, angiostatin, vascular endothelial growth factor-2, myeloid progenitor inhibitory factor-1, osteoprotegerin, α-1-antitrypsin, α-feto proteins, DNase II, kringle 3 of human plasminogen, glucocerebrosidase, TNF binding protein 1, follicle stimulating hormone, cytotoxic T lymphocyte associated antigen 4-Ig, transmembrane activator and calcium modulator and cyclophilin ligand, soluble TNF receptor Fc fusion, glucagon like protein 1 and IL-2 receptor agonist. Antibody proteins, e.g., monoclonal antibodies that may be humanized, are of particular interest. Reporter proteins may be optically detectable or colorigenic, for example. In one embodiment, the protein may be a β-galactosidase (lacZ), β-glucuronidase (GUS), luciferase, alkaline phosphatase, nopaline synthase (NOS), chloramphenicol acetyltransferase (CAT), horseradish peroxidase (HRP) or a fluorescent protein, e.g., green fluorescent protein (GFP), or a derivative thereof, for example.

The avian may be a member of the order Galliformes, e.g., chicken and turkey, Anseriformes, e.g., duck or goose, Charadriiformes, e.g., gulls, button-quails, plovers and allies, Gaviiformes, e.g., loons, Podicipediformes, e.g., grebes, Procellariiformes, e.g., albatrosses and petrels, Sphenisciformes, e.g., penguins, Pelecaniformes, e.g., pelicans, Phaethontiformes, e.g., tropic birds, Ciconiiformes, e.g., storks, Cathartiformes, e.g., New World vultures, Phoenicopteriformes, e.g., flamingos, Falconiformes, e.g., falcons, eagles and hawks, Gruiformes, e.g., cranes and allies, Pteroclidiformes, e.g., sandgrouse, Columbiformes, e.g., doves and pigeons, Psittaciformes, e.g., parrots, Cuculiformes, e.g., cuckoos and turacos, Opisthocomiformes, e.g., hoatzin, Strigiformes, e.g., owls, Caprimulgiformes, e.g., nightjars and allies, Apodiformes, e.g., swifts and hummingbirds, Coraciiformes, e.g., kingfishers, Piciformes, e.g., woodpeckers, Trogoniformes, e.g., trogons, Coliiformes, e.g., mousebirds or Passeriformes, e.g., passerines, for example.

EXAMPLES

The following examples are provided in order to demonstrate and further illustrate certain embodiments and aspects of the present invention and are not to be construed as limiting the scope thereof.

Example 1

Culture of Gonocytes

Embryos were incubated for 7 days, euthanized and the gonad retrieved. The gonads were collected in individual tubes containing 300 µl Ca/Mg free PBS+0.1% BSA. When all gonads were collected, 100 µl of 0.25% trypsin/EDTA was added to each tube and the gonads were incubated@37° C. After 20 minutes the trypsin was neutralized with medium containing serum and the gonad was triturated into single cells and small clumps. The tubes were centrifuged and the supernatant was removed. The tissue of each individual gonad was seeded into a 24 well in growth medium consisting of 40% BRL conditioned KO-DMEM, 47% KO-DMEM, 7.5% fetal bovine serum, 2.5% chicken serum, 2 mM glutamax, 1 mM pyruvate, 1× non-essential amino acids, 0.1 mM beta-mercapto-ethanol. The cultures were incubated at 37° C. and 5% $CO_2$. After 3-5 hours the somatic cells had attached to the bottom of the plate and the gonocytes that were sitting on top of the attached cells were washed off with the medium in the well and transferred to a single 48 well that was preseeded with irradiated BRL cells ($10^5$ cells/$cm^2$). After 24 hours ⅔rds of the medium was removed. Using fresh medium to wash the well, the cells were replated in a new 48 well. Colonies of gonocytes became visible in the 48 wells 2-4 days after the start of culture. Gonocytes were passaged at regular intervals to new wells and expanded.

Example 2

Transfection of Gonocytes with GFP $5×10^6$ gonocytes were pelleted and resuspended in electroporation buffer (V-buffer, Lonza) with 13 µg HS4-bactin-eGFP-CAG-puro and 5 µg cmv-integrase for a final volume of 100 µl. The cells were transferred to a 2 mm electroporation cuvette and electroporated with 8 pulses of 125 µsec at 350V. After electroporation the cells were seeded back into a full 48 well plate on a feeder of BRL cells. After 3 days 1.0 µg/ml puromycin was added to the medium to select the cells in which the construct was incorporated into their genome. When colonies became visible they were transferred to new 48 wells, expanded and injected into recipient embryos.

Example 3

Formation of Chimeras

Chicken embryos were incubated for three days and the egg was opened to reveal the embryo. Stage 13 to 17 Hamburger and Hamilton (1955) embryos with their associated yolk and white were placed under a dissecting microscope and approximately 3000 gonocyte cells from a sustained culture were injected either into the marginal vein, dorsal aorta or the lateral veins. The embryo, yolk and white were then transferred into a surrogate shell. Typically, the surrogate shell was from a chicken egg or a turkey egg that was 25-35 g larger than the egg containing the injected embryo. Surrogate shells were prepared by cutting off the blunt end of the egg as described by van de Lavoir and Mather-Love (2006, Chicken embryonic stem cells: culture and chimera production. Methods in Enzymology 418, 38-64). After pouring the injected embryo, yolk and white into the surrogate shell, 1 ml of a solution containing penicillin and streptomycin was added and the open end was sealed with Saran Wrap glued to the shell with egg white. On the 21st day of development, holes were placed into the Saran Wrap when breathing had commenced. Within the next 12 h, the Saran Wrap was removed and the embryos emerged from the shells.

Example 4

Colonization of the Germline by GFP Expressing Gonocytes

Figure 2A:
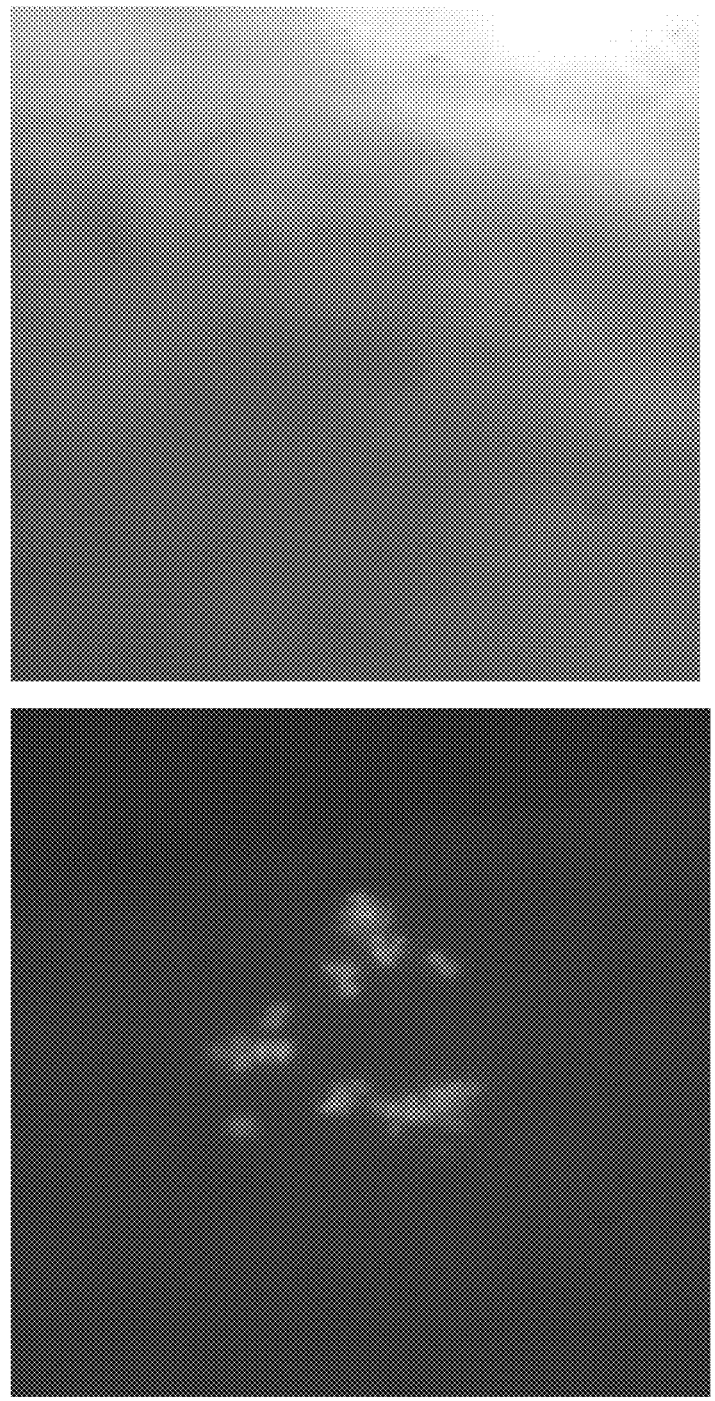
FIGS. 2A and 2B show images of GFP-positive chicken germ cells in a female embryonic quail gonad (FIG. 2A) and GFP-positive chicken germ cells in a female embryonic quail gonad (FIG. 2B).
Figure 2B:
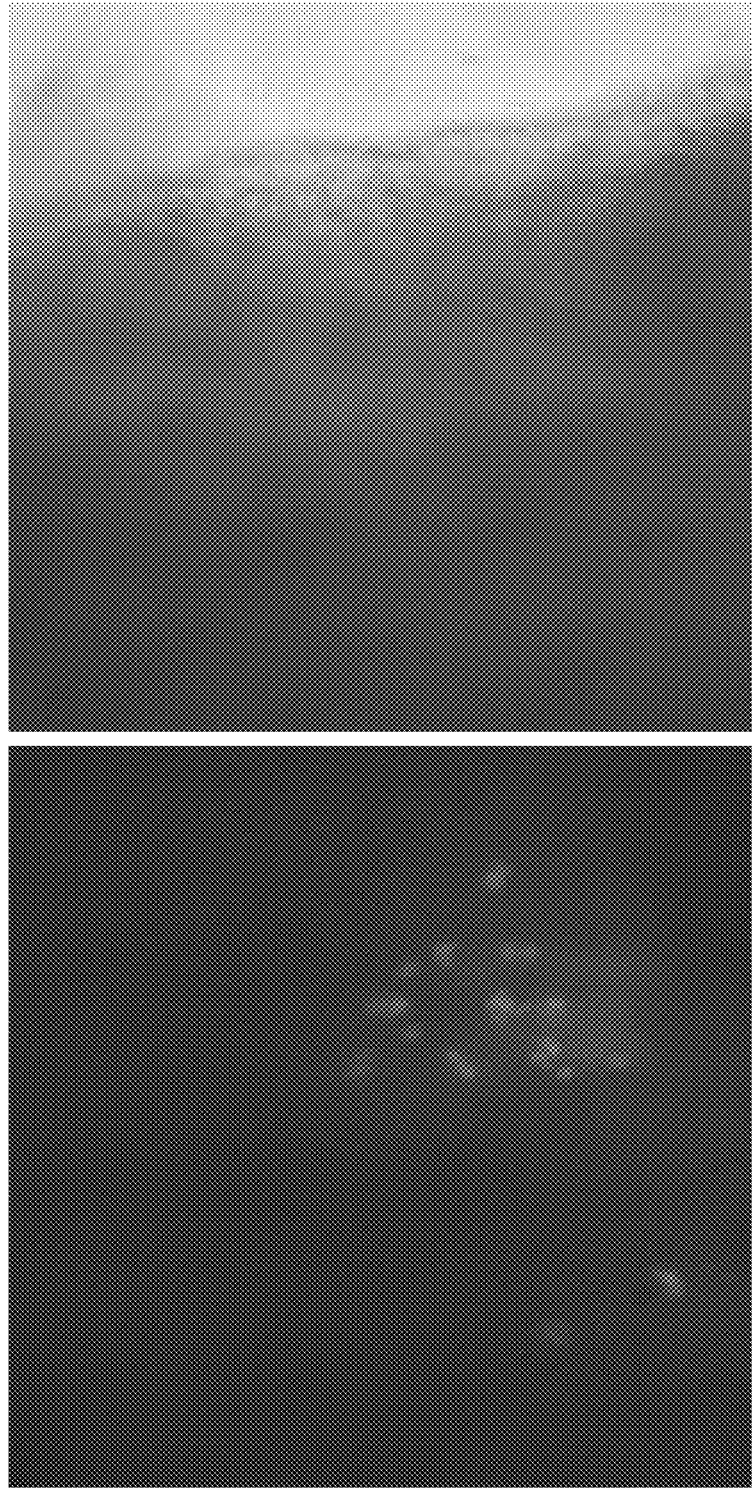

Chimeras were constructed as described in Example 3 using GFP expressing gonocytes that were prepared as described in Example 2. Between the seventh and twentieth day of development or shortly after hatching, the gonads were removed and positioned under a microscope equipped with a fluorescent lamp emitting at a frequency that would reveal GFP. The presence of GFP expressing cells in the gonads is shown in FIG. 1. GFP expressing chickens gonocytes from were also injected into the dorsal aorta of embryonic day 2.5 quail embryos. Gonads were retrieved at 12 days of development and evaluated for the presence of GFP positive cells. FIG. 2A shows a female gonad (K-1m) at 12 days of incubation in which GFP-positive germ cells are incorporated. FIG. 2B shows a male gonad (K15) at 12 days of incubation in which GFP-positive germ cells are incorporated.

What is claimed is:

1. A culture comprising at least $10^4$ genetically identical isolated avian gonocytes that comprise a recombinant nucleic acid inserted in the nuclear genome.

2. The culture of claim 1, wherein the at least $10^4$ genetically identical isolated avian gonocytes comprise an endogenous gene into which a foreign nucleic acid is inserted.

3. The culture of claim 1, wherein the recombinant nucleic acid encodes a protein.

4. The culture of claim 3, wherein the protein is a therapeutic protein.

5. The culture of claim 3, wherein the protein is a selectable marker.

6. The culture of claim 3, wherein the protein provides antibiotic resistance.

7. The culture of claim 1, wherein the recombinant nucleic acid encodes at least part of an antibody.

8. The culture of claim 7, wherein the antibody is a humanized antibody.

9. The culture of claim 1, wherein the cells in the culture are homozygous for the recombinant nucleic acid.

10. The culture of claim 1, wherein the cells in the culture are heterozygous for the recombinant nucleic acid.

11. The culture of claim 1, wherein the culture comprises at least $10^5$ of the genetically identical isolated avian gonocytes.

12. The culture of claim 1, wherein said isolated avian gonocytes are isolated chicken gonocytes.

13. The culture of claim 1, wherein said culture is frozen.

14. A method of making the culture of claim 1 comprising:
   i) isolating gonocytes from the gonad of a 6-10 day old avian embryo;
   ii) culturing the gonocytes;
   iii) transfecting the cultured gonocytes of ii) with a recombinant nucleic acid to produce gonocytes that comprise a recombinant nucleic acid inserted in the nuclear genome; and
   iv) culturing the transfected gonocytes of iii) to provide the culture of avian gonocytes of claim 1.

15. The method of claim 14, wherein the avian embryo is a chicken embryo.

16. The method of claim 14, wherein step iv) comprises passaging the transfected gonocytes onto fresh growth media.

17. A method of using the culture of claim 1, comprising:
harvesting a population of isolated gonocytes from culture of claim 1; and
implanting the population of avian gonocyte cells into a recipient avian embryo.

18. The method of claim 17, wherein the recipient avian embryo is the same species as the gonocytes in the culture.

19. The method of claim 18, further comprising incubating the avian embryo so that the population of isolated gonocytes populate the germ line of the recipient avian embryo.

20. The method of claim 19, further comprising obtaining transgenic offspring of the recipient avian embryo.

21. The method of claim 18, wherein the recipient avian embryo and the gonocytes in the culture are both chicken.

* * * * *